(12) United States Patent
Micali et al.

(10) Patent No.: US 9,038,448 B2
(45) Date of Patent: May 26, 2015

(54) MONITORING APPARATUS, AS WELL AS MONITORING METHOD FOR MONITORING A STATE OF WEAR OF A COMPONENT FOR A RECIPROCATING PISTON INTERNAL COMBUSTION ENGINE

(75) Inventors: Francesco Micali, Winterthur (IT); Matthias Stark, Winterthur (CH); Markus Weber, Volketswil (CH)

(73) Assignee: Wärtsilä Schweiz AG, Winterthur (CH)

( * ) Notice: Subject to any disclaimer, the term of this patent is extended or adjusted under 35 U.S.C. 154(b) by 559 days.

(21) Appl. No.: 13/262,710

(22) PCT Filed: Mar. 25, 2010

(86) PCT No.: PCT/EP2010/053880
§ 371 (c)(1),
(2), (4) Date: Nov. 30, 2011

(87) PCT Pub. No.: WO2010/115716
PCT Pub. Date: Oct. 14, 2010

(65) Prior Publication Data
US 2012/0062894 A1    Mar. 15, 2012

(30) Foreign Application Priority Data
Apr. 6, 2009   (EP) ..................................... 09157425

(51) Int. Cl.
| G01M 15/04 | (2006.01) |
| F01M 11/10 | (2006.01) |
| F01M 1/08 | (2006.01) |
| F16N 29/00 | (2006.01) |
| G01N 33/28 | (2006.01) |
| F01M 11/02 | (2006.01) |

(52) U.S. Cl.
CPC ................. *F01M 11/10* (2013.01); *F01M 1/08* (2013.01); *F01M 2011/022* (2013.01); *F01M 2011/1406* (2013.01); *F01M 2011/1413* (2013.01); *F01M 2011/1453* (2013.01); *F01M 2011/146* (2013.01); *F01M 2011/1473* (2013.01); *F01M 2011/1493* (2013.01); *F16N 29/00* (2013.01); *F16N 2250/30* (2013.01); *F16N 2250/32* (2013.01); *F16N 2250/34* (2013.01); *G01N 33/2888* (2013.01)

(58) Field of Classification Search
USPC ................ 73/114.56, 114.77, 114.78, 116.02
See application file for complete search history.

(56) References Cited

U.S. PATENT DOCUMENTS

| 4,306,525 A | 12/1981 | Faxvog |
| 5,007,284 A * | 4/1991 | Slone .......................... 73/114.78 |
| 5,273,134 A * | 12/1993 | Hegemier et al. .............. 184/6.4 |

(Continued)

FOREIGN PATENT DOCUMENTS

| EP | 1 643 088 A1 | 4/2006 |
| JP | 62-243912 A | 10/1987 |

(Continued)

*Primary Examiner* — Eric S McCall
(74) *Attorney, Agent, or Firm* — Kilpatrick Townsend & Stockton LLP

(57) ABSTRACT

The invention relates to a monitoring apparatus for monitoring a state of wear of a component of a reciprocating piston internal combustion engine wherein an oil collection device is provided for the collection of lubrication oil from the cylinder so that a predetermined measured quantity of lubrication oil is suppliable from the cylinder to a measurement device.

42 Claims, 8 Drawing Sheets

(56) References Cited

U.S. PATENT DOCUMENTS

| | | | |
|---|---|---|---|
| 5,365,773 A * | 11/1994 | Graze et al. | 73/47 |
| 5,633,459 A * | 5/1997 | Rodriguez | 73/114.78 |
| 2001/0013247 A1 | 8/2001 | Wilson et al. | |
| 2007/0074563 A1 * | 4/2007 | Liu et al. | 73/54.24 |
| 2007/0137282 A1 * | 6/2007 | Roby | 73/10 |
| 2012/0042718 A1 * | 2/2012 | Schneider et al. | 73/114.55 |
| 2012/0042719 A1 * | 2/2012 | Schneider et al. | 73/114.55 |

FOREIGN PATENT DOCUMENTS

| | | |
|---|---|---|
| JP | 5-163919 A | 6/1993 |
| JP | 6-94188 A | 4/1994 |
| JP | 2005-299459 A | 10/2005 |
| WO | WO 03/048763 A1 | 6/2003 |

* cited by examiner

MONITORING APPARATUS, AS WELL AS MONITORING METHOD FOR MONITORING A STATE OF WEAR OF A COMPONENT FOR A RECIPROCATING PISTON INTERNAL COMBUSTION ENGINE

CROSS-REFERENCES TO RELATED APPLICATIONS

This application is a National Stage of International Application No. PCT/EP2010/053880, filed Mar. 25, 2010, and which claims the benefit of European Patent Application No. 09157425.1, filed Apr. 6, 2009, the disclosures of which are incorporated herein by reference.

BACKGROUND OF THE INVENTION

The invention relates to a monitoring apparatus, as well as to a monitoring method for monitoring a state of wear of a component of a reciprocating piston internal combustion engine in accordance with the description herein.

Large diesel engines are frequently used as drive aggregates for ships or also in stationary operation, for example, for the drive of large generators for the generation of electrical energy. In this respect the motors run as a rule over considerable time periods in continuous mode of operation which represents high demands on the operational safety and the availability. For this reason, in particular long maintenance intervals, low wear and an economic handling of fuel and operation media are central criteria for the operators for the operation of the machines. Amongst other things the piston running behavior of such large bore slow running diesel engines is a decisive factor for the length of the maintenance intervals, the availability and via the lubricant consumption also directly for the operational costs and thereby for the profitability.

Thereby an always greater significance is given to the complex problem of the lubrication of large diesel engines.

In large diesel engines, however, not only for these, the piston lubrication occurs via lubrication devices present in the piston moving to and fro or within the cylinder wall, by means of which lubrication oil is applied to the running surface of the cylinder wall to minimize the friction between the piston and the running surface and therefore to minimize the wear of the running surface and the piston rings. For example, the wear of the running surface currently lies at less than 0.05 mm for an operational time of a 1000 hours for modern machines such as e.g. the RTA motors of Wärtsilä. The quantity of lubricant conveyed for such engines lies at approximately 1.3 g/kHh and less and at least for reasons of cost should still be reduced as far as possible, wherein the wear should be minimized at the same time.

Very different solutions are known as lubrication systems for lubricating the running surfaces, both with regard to the specific design of the lubrication device itself and also with regard to the method of lubrication. For example, lubrication devices are known in which the lubrication oil is applied through a plurality of lubricant openings onto a piston running past the lubricant openings which are arranged in the circumferential direction in the cylinder wall, wherein the lubricant is distributed through the piston rings both in the circumferential direction and also in the axial direction. In this method, the lubricant is not applied on a large scale onto the running surface of the cylinder wall, but more or less point-wise between the piston rings on the side surfaces of the piston.

Independent of which method is used to apply the lubrication oil onto the counter running partner, specific problems in connection with the cylinder lubrication and, in particular in connection with the wear of the components of cross-headed large diesel engines exist which up until today have remained unresolved.

In this respect it is known to at least coarsely determine the state of wear of pistons, piston rings, gas exchange valves, such as e.g. the outlet valve, the running surface and other components of the internal combustion in that specific properties of the lubrication oil used in the internal combustion engine are investigated. For this purpose the lubrication oil which, for example, collects at the bottom of the piston bottom side space in the case of longitudinal scavenged two-stroke large diesel engines, is collected in a container and the collected lubrication oil is investigated, for example, on the presence of iron particles. When a certain quantity of iron is then determined in the thereby collected lubrication oil this permits certain crude conclusions on the state of wear of the aforementioned cylinder components. In this respect the measurement of the iron content occurs in a manner known per se by means of a magnetic method.

These known methods, however, have a series of disadvantages which frequently severely distort the measurement results in practice.

For example, the lubrication oil which has settled, for example, at the floor of the piston bottom side space, is contaminated with many other materials which did not originally emerge from the combustion space of the internal combustion engine. For example, contaminants are transported into the receiver space from the turbo charge system which additionally contaminates the lubrication oil. Naturally, a certain quantity of contaminated lubrication oil is also always conveyed from the crankshaft space into the piston bottom side space through the stuffing boxes. Moreover, the lubrication oil stored in the receiver space is always a mixture of contaminated lubrication oil which is composed of very many past engine cycles, so that the lubrication oil settled in the receiver space never represents a current composition of the lubrication oil, as it corresponds to the current real composition of the lubrication oil in the cylinder liner.

This means that the lubrication oil settled in the receiver space includes a whole series of residues which either do not stem from the corresponding cylinder liner and/or do not correspond to the current situation.

A further grave disadvantage of the known measurement methods lies therein that the magnetic measurement systems used have a far too small a sensitivity. This has the effect that a comparatively large quantity of lubrication oil has to be collected. The lubrication oil is typically collected in a container which has a volume of a few 10 cm$^3$ which has to be more or less completely filled before a measurement can actually be carried out. The lubrication oil consumption of, for example, a modern large diesel engine has been strongly minimized as was initially mentioned, so that it typically takes many hours until a sufficient quantity of lubrication oil has been collected, which can then be investigated in the known measurement systems.

The disadvantages are obvious. Real online measurements in the sense that a current state of wear of the engine components can be determined are not at all possible, as a measurable sample of lubrication oil has to be collected over a long period. This has the effect that, for example, a starting seizure of the piston at the cylinder running surface, i.e. the feared scuffing, is frequently only noticeable too late. Frequently only so late that massive damage at the cylinder components can no longer be avoided. The result is that a cylinder liner has to frequently be taken out of operation and be replaced.

BRIEF SUMMARY OF THE INVENTION

For this reason it is an object of the invention to provide an improved monitoring apparatus for monitoring a state of wear of the component of a reciprocating piston internal combustion engine with which a state of wear of components of the internal combustion engine can be monitored reliably and fast, preferably in a real online measurement method, possibly in real time, so that corresponding measures, such as, for example, maintenance measures or a corresponding matching of the control of the machine or the cylinder in question can be carried out without unnecessary time delays.

The invention therefore relates to a monitoring apparatus and to a monitoring method for monitoring a state of wear of a component of a reciprocating piston internal combustion engine including a cylinder having a cylinder cover and a running surface provided at a cylinder wall of the cylinder in which cylinder a piston is arranged movable to and fro in an axial direction along the running surface between a bottom dead center and a top dead center such that the piston, the cylinder cover and the cylinder wall form a combustion space in the cylinder for the combustion of a mixture of fuel and air wherein an oil collection device is provided for the collection of lubrication oil from the cylinder, so that a predetermined measured quantity of lubrication oil is suppliable from the cylinder to a measurement device. In accordance with the invention the measured quantity of lubrication oil is directly supplied from the running surface of the cylinder and/or is directly suppliable from the combustion space and/or is directly suppliable from a piston ring package of the piston to the collection device.

The fact that the measurement quantity of lubrication oil no longer consists of lubrication oil settled and collected in the receiver space, but only lubrication oil is used for the measurement which directly and currently stems from the cylinder space and therefore is not contaminated with foreign materials means that the lubrication oil collected in accordance with the invention substantially only includes such information which reflects the current state of wear of the cylinder components, such as pistons, piston rings, cylinder running surface, gas exchange valve etc.

For this reason it is possible for the first time to monitor the current state of wear of the motor components, without interfering foreign influences, such as, for example, contaminations which do not directly stem from the cylinder liner or do not correlate with the point in time of the measurement.

To carry out real time measurements as far as possible, it is preferred to preferably use a fast measurement method as is disclosed herein. The fastest measurement method in accordance with the invention is therefore suitable to carry out measurements on a motor, in particular also such that measurements can be carried out on a motor which is currently in the transient operating state, wherein the transient operating state relates to an engine number of rotations which changes during the measurement or to an engine load which changes during the measurement or to a combination of engine numbers of rotations and engine load changing during the measurement.

A particularly advantageous embodiment of a fast measurement method which is also cost-effective and simple from the apparatus point of view and which, in particular only requires very small quantities of lubrication oil for a measurement, essentially uses a measurement capacitor which is geometrically designed such that the quantity of lubrication oil collected during a single or at least during a very few number of combustion cycles is sufficient to fill the capacitor with a measurable quantity of lubrication oil.

For example, a capacitor, e.g. a plate capacitor, having a small plate separation distance can be used.

A cylindrical plate capacitor can also be used very advantageously which comprises two spiral-like metal surfaces wound into one another which are arranged as close as possible to one another.

The collected lubrication oil can then be blown into the cylindrical plate capacitor for the measurement and a measurement can thenbe carried out. Following the conclusion of the measurement, the cylindrical capacitor can be cleaned, for example with pressurized air, so that in a next cycle newly collected lubrication oil can be blown into the cylindrical capacitor for a further measurement.

Using a measurement bridge as known per se, for example, the complex conductance, can then be measured, preferably still in dependence of frequency and/or of temperature or in dependence of the applied electrical voltage, of the temperature or of the variation of other parameters. Conclusions can thenbe directly drawn on the contaminants, such as water, metals such as iron, chromium, vanadium or other metals from the measurement values, for example, by means of a comparison with calibration measurements or by means of the evaluation of suitable mathematical functions. Conclusions can also be drawn on chemical contaminants, in particular on irons forming contaminants or components, such as acids or bases etc. so that also changes in the chemical composition are accessible and, for example, element concentrations of sulfur, phosphor or other chemical elements or components can be determined.

The capacitor can be used, for example in an electric circuit in a manner known per se, which electric circuit also includes a coil of predefined conductivity and thereby forms an oscillating circuit of predetermined resonant frequency beside other electric components for increasing the measurement accuracy and thus ultimately also for the reduction of the required measurement volume of lubrication oil.

Such arrangements react to a change of the inductivity of the coil or of the dielectric constant of the capacitors extremely sensitively by means of a change of the resonance frequency. Thereby an extremely sensitive measurement instrument is made available by means of which a very high measurement accuracy can be achieved also in regard to different ingredients and also with a very small sample volume by means of the present invention having such an arrangement, wherein also a plurality of oscillating circuits of different resonant frequencies can be coupled.

In this respect it is naturally understood that the lubrication oil can also be filled into a suitable constructed coil which leads to a change of the inductivity in dependence on the contamination. Naturally, also a correspondingly prepared capacitor or a correspondingly prepared coil can be combined in a measurement circuit.

Furthermore, also other dimensions, such as, for example the measurement frequency or the measurement amplitude can be suitably used, to e.g. increase the measurement accuracy or to utilize certain phenomena such as, for example, resonance appearances. Thus, for example, an electric or a differently operated heating can be provided at the measurement body, i.e. for example, a capacitor filled with oil so that a measurement can be carried out with a defined temperature, in which, for example, a certain relaxation process can be measured particularly well. Further corresponding methods of manipulation are known to the person of ordinary skill in the art by means of whose use interesting dimensions can be particularly well determined.

It is naturally understood that for improving the measurement accuracy, for example, also other dimensions can be determined by means of suitable sensors which are generally known per se. Thus, for example, sensors can be provided which monitor the temperature during the measurement or which automatically monitor the quantity of lubrication oil which is available for a current measurement, so that the direct measurement size can be correspondingly corrected if necessary.

The lubrication oil is preferably collected through suitable openings in the cylinder wall, so that samples can be taken in dependence of position and/or of time. This can occur, for example thereby, that lubrication oil is supplied through the openings in the cylinder wall to a collection system and/or measurement system due to the over-pressure present in the cylinder and/or the ring package with regard to the environment. The mentioned over-pressure present in the ring package with regard to the environment results both for a reciprocating piston engine according to the two-stroke construction type and also in accordance with the four-stroke construction type, so that the measurement principle in accordance with the invention can be used both for two-stroke reciprocating piston motors and also for four-stroke reciprocating piston motors.

However, also an extraction of lubrication oil via the scavenging slits is advantageously possible. When the piston passes the scavenging slits which open into the receiver space on its movement in the direction toward the bottom dead center, the lubrication oil from the piston ring grooves and/or from the piston ring packages, in which a certain quantity of lubrication oil is always stored, are blown into the receiver space in the form of a lubrication oil cloud, by means of the over-pressure present in the piston ring package, the lubrication oil is then collected in the receiver space from the lubrication oil cloud by means of a suitable collection device.

As is known to the person of ordinary skill in the art the gas pressure runs through the piston ring package like in a labyrinth seal and is stored there together with the lubrication oil present in the piston ring package and can then practically not escape as long as the piston ring package lies sealingly at the running surface of the cylinder wall. If the piston then passes the scavenging slits on its decompression movement in the direction toward the bottom dead center UT, then the gas stored in the piston ring package together with the lubrication oil stored in the piston ring package can escape abruptly into the receiver space via the scavenging slits in the form of a lubrication oil cloud, whereby the receiver space is naturally massively contaminated with lubrication oil.

This generally negative side effect can thereby be positively exploited by means of the invention.

However, the condition can arise that the gas pressure in the piston ring package no longer lies substantially above the environmental pressure at the end of the expansion stroke following the combustion for non-turbocharged reciprocating piston engines in accordance with the two-stroke construction type and the four-stroke construction type and thus no sufficiently large quantity of oil would arise with the oil collection device in accordance with the invention. This circumstance can be remedied in that an under-pressure can be plastically applied from the outside which can, for example, be brought about by a blower on the exit air side of the used oil/air separator. From this a sufficiently large pressure difference again results between the ring package and the exit air side of the used oil/air separator, whereby the function of the oil collection system and the measurement system is also ensured for non-turbocharged reciprocating piston motors.

In a preferred embodiment of a monitoring apparatus in accordance with the invention the oil collection device includes an oil collection opening which is provided at the cylinder wall between the bottom dead center of the piston and the cylinder cover. In this respect the oil collection device, in particular includes an oil collection valve actuatable by a control device.

In this respect the reciprocating piston internal combustion engine can be both a longitudinally scavenged internal combustion engine with scavenging slits, in particular a slow running two-stroke large diesel engine, wherein the oil collection opening is preferably arranged in the region of the scavenging slits such that lubrication oil exiting via the scavenging slits is collectable to the oil collection opening. In this respect it is naturally understood that the reciprocating piston internal combustion engine can also be an internal combustion engine which is operated on the four-stroke principle.

When the reciprocating piston internal combustion engine is a four-stroke reciprocating piston internal combustion engine the oil collection openings are preferably arranged at the cylinder between the piston of a crown of the piston in the top dead center and the position of a bottom side of a piston in the bottom dead center, such that lubrication oil is collectable from the cylinder through the oil collection opening. Suitable oil openings of the oil collection device at the cylinder particularly preferably lie between the position of the piston crown in the top dead center and the lowest ring of the piston ring package of the piston in the bottom dead center. It can, in particular be ensured that lubrication oil is collectable essentially from the overall running surface of the piston rings of a four-stroke engine relevantly wetted through the oil collection device by means of such an arrangement of the openings of the oil collection device of the cylinder wall.

The oil collection device particularly preferably includes an oil collection space which is preferably an integral part of the cylinder wall, wherein the lubrication oil collected in the oil collection space is suppliable to the measurement apparatus via the oil collection opening.

Frequently at least two oil collection openings are provided which are arranged at the cylinder displaced from one another in the circumferential direction and/or with regard to the axial direction, wherein the oil collection opening is designed such that a lubrication oil flow rate is settable in a particular embodiment.

In this respect the measurement system advantageously includes an electromagnetic measurement unit, in particular a measurement unit for the amplitude dependent and/or the frequency dependent and/or the frequency independent determination of a capacitance, of a magnetic permeability, of an electric conductivity and/or of an AC conductivity and/or of a complex electric conductivity and/or of a complex electric resistance of the collected measured quantity of lubrication oil, wherein the monitoring apparatus can preferably be provided miniaturized directly in the cylinder wall.

In a different embodiment of the present invention, the measurement device includes an X-ray measurement unit, in particular for the determination of a transmission property and/or of an absorption property and/or of a reflection property and/or of a fluorescence property of the collected measured quantity of lubrication oil.

In a further embodiment the measurement system includes an optical measurement unit for the determination of an optical transmission property and/or of an optical absorption property and/or of an optical reflection property and/or of an optical fluorescence property of the collected measured quantity of lubrication oil, wherein the optical measurement unit is preferably an infrared measurement unit and/or an ultraviolet measurement unit.

In practice, the measurement system can, in particular, be a chemical measurement device for the determination of a chemical composition of the collected measured quantity of lubrication oil, wherein the measurement system includes a measurement device for the determination of a content of water and/or of a content of metal, in particular of iron and/or or chromium and/or of vanadium, and/or for the determination of a content of phosphor and/or of sulfur of the collected measured quantity of lubrication oil.

The invention further relates to a reciprocating piston internal combustion engine, in particular to a two-stroke large diesel engine or to a four-stroke engine having a monitoring apparatus in accordance with the invention, as well as to a monitoring method for monitoring a state of wear of a component of a reciprocating piston internal combustion engine.

The monitoring method in accordance with the invention relates to a monitoring method for monitoring a reciprocating piston internal combustion engine including a cylinder having a cylinder cover and a running surface provided at a cylinder wall of the cylinder, in which cylinder a piston is arranged movable to and fro in an axial direction along the running surface between a bottom dead center and a top dead center such that the piston, the cylinder cover and the cylinder wall form a combustion space in the cylinder for the combustion of a mixture of fuel and air. In this respect an oil collection device is provided for the collection of lubrication oil from the cylinder and, in the operating state, a predetermined measured quantity of lubrication oil is supplied from the cylinder to a measurement device. In accordance with the invention the measured quantity of lubrication oil is directly supplied from the running surface of the cylinder and/or is directly supplied from the combustion space and/or is directly supplied from a piston ring package of the piston to the oil collection device.

For carrying out the monitoring method in accordance with the invention, the oil collection device preferably includes an oil collection opening which is provided at the cylinder wall between the bottom dead center of the piston and the cylinder cover.

The oil collection device, in particular includes an oil collection valve actuatable by a control device, so that in the operating state a predefined quantity of lubricant can be led away out of the cylinder.

In this respect the reciprocating piston internal combustion engine, for example, is a longitudinally scavenged internal combustion having scavenging slits, in particular is a slow running two-stroke large diesel engine and the oil collection opening is arranged in the region of the scavenging slits such that lubrication oil exiting via the scavenging slits is collected through the oil collection opening in the operating state. It is naturally understood that the monitoring method in accordance with the invention can naturally also be successfully used for an internal combustion engine which is operated in accordance with the four-stroke principle.

The oil collection device particular preferably includes an oil collection space for carrying out the monitoring method in accordance with the invention, which oil collection space is preferably an integral part of the cylinder wall, so that lubrication oil collected in the oil collection space is suppliable to the measurement device, in particular can also be supplied via the oil collection openings.

In practice generally at least two oil collection openings are provided which are arranged at the cylinder displaced from one another in the circumferential direction and/or with regard to the axial direction, so that samples of lubrication oil can be taken from different positions in the cylinder, wherein the oil collection opening is preferably designed such that a lubrication oil flow-rate can be set, preferably such that a lubrication oil flow-rate can be set automatically.

For carrying out the monitoring method in accordance with the invention, the measurement system particularly preferably includes an electromagnetic measurement unit so that, in particular an amplitude dependent and/or a frequency dependent and/or a frequency independent determination of a capacitance, of a magnetic permeability, of an electric DC conductivity and/or of an AC conductivity, and/or of a complex electric conductivity and/or of a complex electric resistance of the collected measured quantity of lubrication oil is carried out.

In a further embodiment, the measurement system includes an X-ray measurement unit so that, in particular a determination of a transmission property and/or of an absorption property and/or of a reflection property and/or of a fluorescence property of the collected measured quantity of lubrication oil is carried out.

In a further specific embodiment, the measurement system includes an optical measurement unit, so that in particular a determination of an optical transmission property and/or of an optical absorption property and/or of an optical reflection property and/or of an optical fluorescence property of the collected measured quantity of lubrication oil can be carried out, wherein an infrared measurement unit and/or an ultraviolet measurement unit is preferably used as the optical measurement unit.

In practice the measurement system frequently includes a chemical measurement unit, so that a determination of a chemical composition of the collected measured quantity of lubrication oil can be carried out, wherein a content of water and/or a content of metal, in particular of iron and/or of chromium and/or of vanadium and/or a content of phosphor and/or of sulfur of the collected measured quantity of lubrication oil is particularly preferably determined with the measurement unit.

The data recorded with the measurement device are evaluated, in particular are evaluated by means of a look-up table and/or by means of a predetermined mathematical function and/or by means of a calibration, wherein, in particular a state of wear of a component of the reciprocating piston internal combustion engine, in particular the state of wear of the piston and/or of a piston ring and/or of the running surface of the cylinder wall and/or of a gas exchange valve and/or of a different engine component is determined.

An evaluation of the measurement of the collected measured quantity of lubrication oil is particularly preferably carried out for each engine cycle, wherein a predetermined measured quantity of lubrication oil is particularly preferably collected during a predetermined number of engine cycles and a measurement is carried out and evaluated on the predetermined measured quantity of lubrication oil.

Through an evaluation of the complete measurement data, for example, a maintenance point in time for the maintenance of a predefined engine component is preferably automatically determined.

The reciprocating piston internal combustion engine can naturally also be controlled and/or regulated in dependence on a measurement result of the collected measured quantity of lubrication oil.

A specific embodiment of the present invention which is particularly relevant for practice is a "self-regulating lubrication system", i.e. an essentially electronically regulated lubrication system which ensures very homogeneous and efficient properties of the oil film, which at the same time reduces the loads on the oil film and prevents a degradation of the oil film, both in the circumferential direction and also in the axial direction of the cylinder liner and indeed under all operating conditions.

The present invention thereby focuses on the constant new adjustment of the operating parameters of the lubrication system, such as, for example, the lubrication oil feed rate, the vertical and/or horizontal distribution of the lubrication oil, the injection frequency etc. if the corresponding lubrication film properties no longer correspond to or fall below or above predefined parameter boundaries. Furthermore, the quality and/or the performance of the lubrication and the lubrication oil film is dependent on the operating conditions under which the internal combustion engine is operated, such as, for example, the load, the humidity of the scavenging air, the sulfur content in the fuel, the fuel quality, the quality of the lubrication oil etc.

If, for example, two or more oil collection openings are provided at the cylinder which are displaced from one another in an axial direction and/or in a circumferential direction then it is possible to, for example, collect lubrication oil directly from the piston main package or from the running surface of the cylinder liner at different position of the cylinder, to analyze the lubrication oil and from that to generate a type of "map" of the distribution of the properties of the lubrication oil film over the overall running surface of the cylinder by means of the measurement device in accordance with the invention. The supply of lubrication oil onto the running surface of the cylinder can then be controlled and/or regulated in dependence of time and/or of position from the thereby obtained measurement data via a suitable control and/or regulation, such that a uniform performance and quality of the lubrication oil film is permanently and automatically ensured over the overall running surface of the cylinder.

As is schematically shown with reference to FIG. 1, lubrication oil 9 is preferably separately collected from an upper region OB at a first oil collection opening 81 and at a lower region UB at a second oil collection opening 81 of a cylinder 3 and the properties of the thereby collected lubrication oil 9, such as, for example, alkalinity (BN-value), the iron content, the water content etc. can be separately analyzed in the two measurement devices M1 and M2 and be supplied to a data processing plant DV having the data acquisition unit. In the present example the lower second oil collection opening 81 lies in the region of the scavenging slits 11, so that lubrication oil 9 is collected from the piston ring package through the lower second oil collection opening 81, while the upper first oil collection opening collects lubrication oil directly from the running surface of the cylinder 3.

In this respect the cylinder 3 has a plurality of lubrication oil nozzles provided in a manner known per se, which for reasons of clarity are not illustrated in FIG. 1, by means of which fresh lubrication oil can be applied onto the running surface 51 of the cylinder 3 in a predefined scheme. In this respect the plurality of lubrication oil nozzles are provided both in the circumferential direction and also in the vertical direction at the cylinder 3 spaced apart from one another.

The data processing plant DV determines new supply parameters ZP for the lubrication oil, such as, for example, the quantity of lubrication oil, the frequency of supply of the lubrication oil into the cylinder etc., from the separately measured properties of the lubrication oil 9 of the piston ring package of the piston 6 in the cylinder liner 3 in dependence on the position of the cylinder liner 3, whereby a deviation of the lubrication oil film from the predefined nominal value parameters are compensated again, so that the lubrication oil film can be optimized at every point in time and at every position on the running surface 51 of the cylinder 3 by means of the invention. The so newly determined new supply parameters ZP are further provided to a lubrication oil controller SK, which sets the further supply of the lubrication oil 9 via the plurality of lubrication nozzles, so that the lubrication oil film is optimized on the overall running surface 51 of the cylinder 3 as described before.

It is important in the specific embodiment in accordance with FIG. 1 that lubrication oil 9 is separately collected and analyzed from the upper region OB of the cylinder 3 and from the lower region UB of the cylinder 3. The lubrication oil 9 which is collected in the upper region OB of the cylinder 3, for example, directly stems from the running surface 51. Thereby it can be ensured that the oil collection opening 81 in the upper region OB of the cylinder 3 takes a sample of lubrication oil 9 when the piston 6 does not pass the upper oil collection opening 81. By contrast the lower oil collection opening 81 at the scavenging slits 11 then collects exactly a sample of lubrication oil 9 then when the piston 6 passes the scavenging slits 11. Thereby the sample of lubrication oil 9 which is collected in the lower region UB of the cylinder 3 directly stems from the piston ring package of the piston 6, as the over-pressure in the piston ring package is discharged through the scavenging slits 11 and thus, lubrication oil 9 collected in the piston ring package is blown out of the piston ring package, so that a sample of lubrication oil 9 can be taken from the lubrication oil 9 then blown out of the piston ring package through the oil collection opening 81 in the lower region UB.

If, for example, the BN-value of the lubrication oil in the cylinder should be optimized, this can be achieved in the following manner. The BN-value of the lubrication oil is, as is well known to the person of ordinary skill in the art, a measure of the alkaline behavior of the lubrication oil, i.e. a measure for its alkalinity. In this respect the lubrication oil must have a certain alkalinity, since very aggressive acids can arise in the cylinder, for example, due to the combustion process, which acids have to be neutralized as much as possible, so that these acids do not attack the individual components in the cylinder, such as piston, running surface, piston rings, outlet valve etc. as far as possible.

For this reason a minimum BN-value of the lubrication oil in the cylinder is required which can depend on the specific motor, the operating conditions and other operating parameters.

In this respect in a specific embodiment of the monitoring method in accordance with the invention, the BN-value, for example, for the lubrication oil collected in the piston ring package is initially regulated to a predefined minimum BN-value which, for example, can have the predefined nominal value BN=5. This predefined nominal value BN=5 can naturally have a very different value than BN=5 in a different motor or for different operating conditions.

In this respect the predefined minimum nominal value of, for example, BN=5 should essentially not be exceeded if possible, as the nominal value is also a measure for the quantity of supplied lubrication oil, which for reasons of cost alone should simultaneously be optimized and/or minimized. As the lubrication oil present in the piston ring is collected over the overall height of the cylinder liner from the running surface on an expansion stroke, the BN-value represents a specific mean value of a distribution of the BN-values over the height of the running surface in the axial direction of the lubrication oil stemming from the piston ring package.

For this reason, the BN-value can essentially be uniformly set over the height of the cylinder liner in the vertical direction along the cylinder axis, in that it is attempted to set the BN-value of the lubrication oil, which stems from the upper region of the cylinder as identical as possible to the BN-value of the lubrication oil which is blown out from the piston ring package in the region of the scavenging slits. Ideally the BN-value of the lubrication oil from the upper region of the cylinders is equal to the BN-value of the lubrication oil from the piston ring package as it is measured in the region of the scavenging slits. In this case the BN-value along the cylinder axis must be essentially equal.

In this respect the regulation of the BN-value occurs through the setting of the supply parameters, i.e. through the regulation of the supply of the lubrication oil via the lubrication oil nozzles, which are preferably actuatable individually or separately in respective specific groups.

It is naturally understood that because a plurality of oil collection openings are also provided in the circumferential direction of the cylinder liner, the BN-value can also be set uniformly, i.e. homogeneously, in the circumferential direction.

Thus, it is possible for the first time that the BN-value of the lubrication oil can be uniformly set to essentially the same value on the overall running surface of the cylinder, both in the circumferential direction and also in the vertical direction by means of the invention, wherein a minimization and an optimization of the lubrication oil consumption is additionally achieved, since it is also simultaneously regulated to a predefined optimum BN-value of, for example BN=5.

It is naturally understood that also other parameters of lubrication oil can be optimized completely analogously to a predefined value in an analog manner, by means of the invention homogeneously over the running surface.

Furthermore, it is naturally immediately clear to the person of ordinary skill in the art that the above-described steps of the optimization method are to be understood merely by way of example and that, in particular the steps can also occur in a different sequence, or that additional steps can be introduced, or that in other simple cases specific optimization steps can also be omitted.

The invention further relates to a measurement device for determining a composition of a fluid, in particular of an oil, specifically of a lubrication oil or a fuel for a reciprocating piston internal combustion engine. In this respect the measurement device in accordance with the invention includes an electromagnetic measurement unit, in particular a measurement unit for the amplitude dependent and/or the frequency independent determination of a capacitance, of a magnetic permeability, of an electric DC conductivity and/or of an AC conductivity, and/or of a complex electric conductivity and/or of a complex electric resistance of a predefined measured quantity of the fluid.

In a different embodiment the measurement device can include an X-ray measurement unit, in particular for the determination of a transmission property and/or of an absorption property and/or of a reflection property and/or of a fluorescence property of the measured quantity of fluid.

In a further embodiment the measurement device can include an optical measurement unit for the determination of an optical transmission property and/or of an optical absorption property and/or of an optical reflection property and/or of an optical fluorescence property of the measured quantity of fluid, wherein the optical measurement unit is preferably an infrared measurement unit and/or an ultraviolet measurement unit.

In practice the measurement device frequently includes a chemical measurement unit for the determination of a chemical composition of the collected measured quantity of the fluid, wherein, in a specific embodiment, the measurement system is a measurement device for the determination of a content of water and/or of a content of metal, in particular of iron and/or of chromium and/or vanadium, and/or is a measurement device for the determination of a content of phosphor and/or sulfur of a collected measured quantity of the fluid.

The invention further relates to a measurement method for determining a composition of a fluid, in particular of an oil, specifically of a lubrication oil or of a fuel for a reciprocating piston internal combustion engine. In this respect in accordance with the invention a measurement device is used which measurement device includes an electromagnetic measurement unit, so that in particular an amplitude dependent and/or a frequency dependent and/or a frequency independent determination of a capacitance, of a magnetic permeability, of an electric DC conductivity and/or of an AC conductivity and/or of a complex electric conductivity and/or of a complex electric resistance of the collected measured quantity of lubrication oil can be carried out.

In a different embodiment of the measurement method in accordance with the invention the measurement device includes an X-ray measurement unit, so that, in particular a determination of a transmission property and/or of an absorption property and/or of a reflection property and/or of a fluorescence property of the measured quantity of fluid can be carried out.

In a further embodiment, the measurement device includes an optical measurement unit as an electromagnetic measurement unit so that, in particular a determination of an optical transmission property and/or of an optical absorption property and/or of an optical reflection property and/or of an optical fluorescence property of the measured quantity of fluid can be carried out, wherein an infrared measurement unit and/or an ultraviolet measurement unit is preferably used as the optical measurement unit.

In an embodiment particularly relevant for practice, the measurement device includes a chemical measurement unit, so that a determination of a chemical composition of the measured quantity of fluid can be carried out, wherein a content of water and/or a content of metal, in particular of iron and/or of chromium and/or of vanadium, and/or a content of phosphor and/or of sulfur of the collected measured quantity of fluid is particularly preferably determined with the measurement device.

Specifically the data recorded with the measurement device is evaluated, in particular is evaluated by means of a look-up table and/or by means of a predetermined mathematical function and/or by means of a calibration and consequently a state of wear of a component with the reciprocating piston internal combustion engine is determined therefrom, in particular the state of wear of the piston and/or of a piston ring and/or of the running surface of the cylinder wall and/or of a gas exchange valve and/or of a different engine component is determined.

In a preferred embodiment an evaluation of the measurement of the collected measured quantity of fluid is carried out for each engine cycle or, however, a predetermined measured quantity of fluid is collected during a predetermined number of engine cycles and a measurement is carried out and evaluated on the predetermined measured quantity of fluid.

On use of a measurement method of the present invention, for example, a maintenance point in time for the maintenance of a predefined engine component, can also be preferably automatically determined, or the reciprocating piston internal combustion engine can also be controlled and/or regulated in dependence on a measurement result of the collected measured quantity of lubrication oil.

BRIEF DESCRIPTION OF THE DRAWINGS

In the following the invention will be explained in more detail with reference to further drawings. There is shown in schematic illustration.

DETAILED DESCRIPTION OF THE INVENTION

Figure 1:
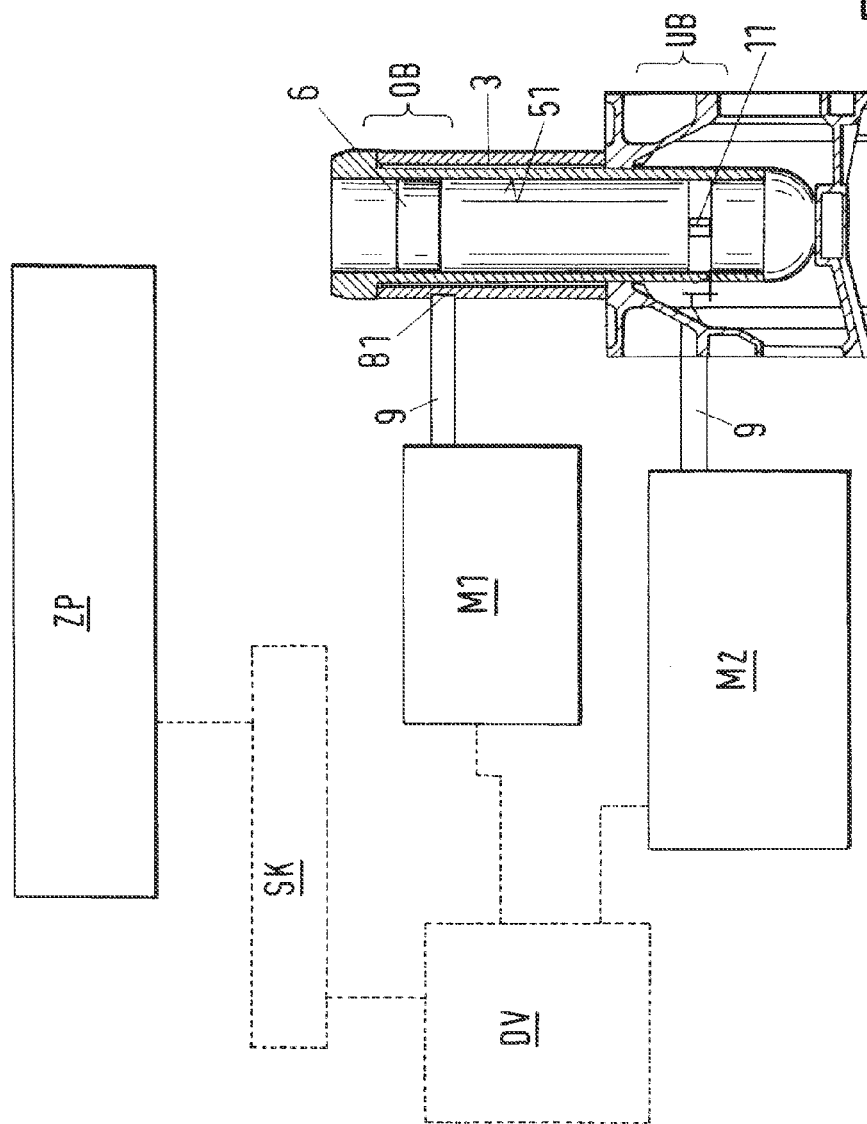
FIG. 1 is an apparatus for optimizing the lubrication oil film on the cylinder running surface.

As FIG. 1 has already been discussed above in detail one can proceed directly with the description of FIG. 2 in the following.

A first simple embodiment of a monitoring apparatus in accordance with the invention is schematically illustrated with reference to FIG. 2 which will be referred to overall using the reference numeral 1 in the following.

Figure 2:
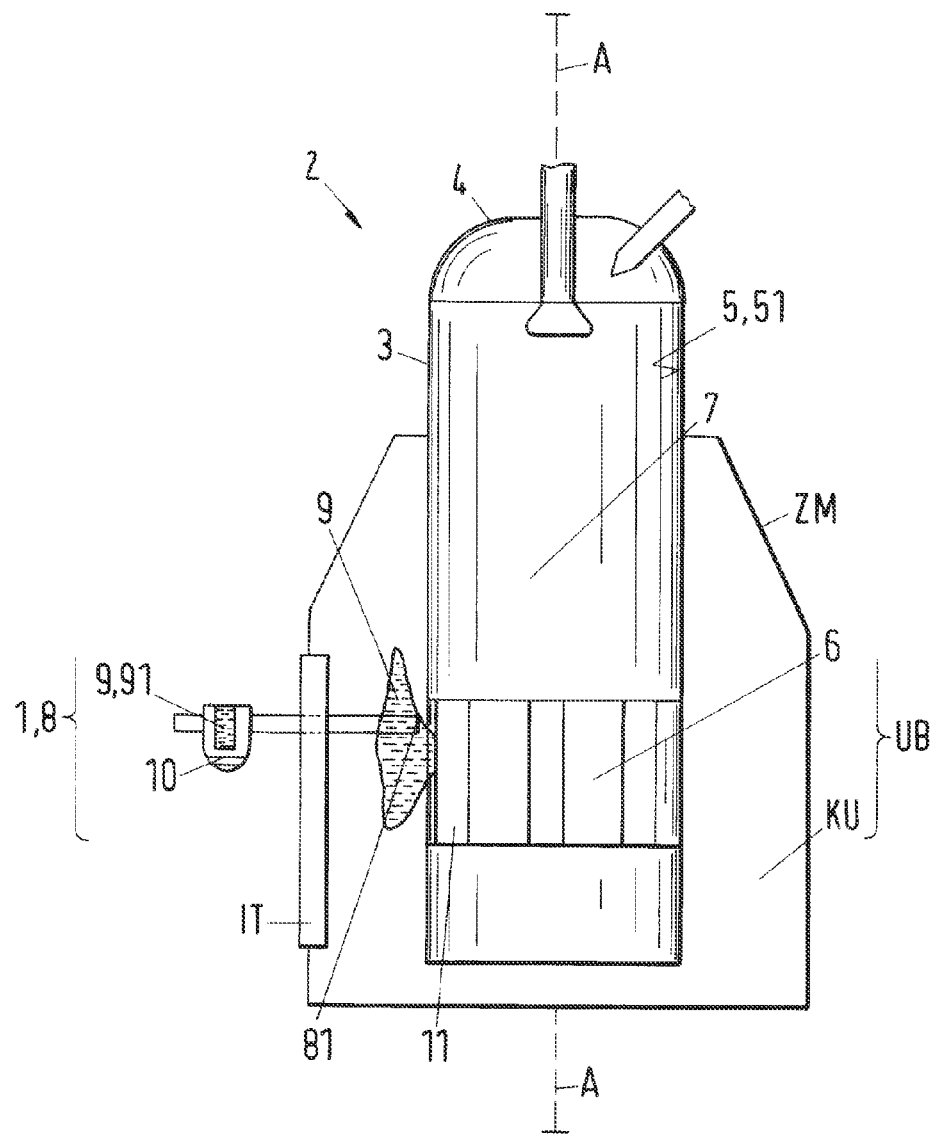
FIG. 2 is a first simple embodiment of a monitoring apparatus in accordance with the invention.

The monitoring apparatus 1 of FIG. 2 for monitoring a state of wear of a component of a reciprocating piston internal combustion engine 2 includes a cylinder 3 having a cylinder cover 4 and a cylinder running surface 51 provided at a cylinder wall 5 of the cylinder 3. A piston 6 is arranged movable to and fro in an axial direction A along the running surface 51 between a bottom dead center and a top dead center, such that the piston 6 the cylinder cover 4 and the cylinder wall 5 form a combustion space 7 for the combustion of a mixture of fuel and air in the cylinder 3. In this respect an oil collection device 8 is provided for the collection of lubrication oil 9 from the cylinder 3, so that a predetermined measured quantity 91 of lubrication oil 9 is suppliable from the cylinder 3 to a measurement device 10. In this respect only one oil collection device 8 is exemplary provided in a lower region UB of the cylinder 3 in the region of the scavenging slit 11 in the present simple embodiment of FIG. 2. In FIG. 2 the piston 6 is currently in the region of the scavenging slit 11. As can clearly be seen the cloud of lubrication oil 9 which is blown out from the piston ring package of the piston 6 through the scavenging slits 11 into the space of the cylinder mantle ZM, which space of the cylinder mantle ZM is accessible via the inspection door IT in a manner known per se. The reference numeral KU refers to the vertical region of the piston bottom side. Here the measured quantity 91, i.e. a lubrication oil sample 91 of lubrication oil 9 is directly supplied from the piston ring package of the piston 6 to the oil collection device 8 and is analyzed by an analysis and control system, as is, for example, explained with reference to FIG. 1 and with the aid of the results of this analysis the lubrication oil supply into the cylinder 3 can then be regulated and/or controlled.

Figure 3:
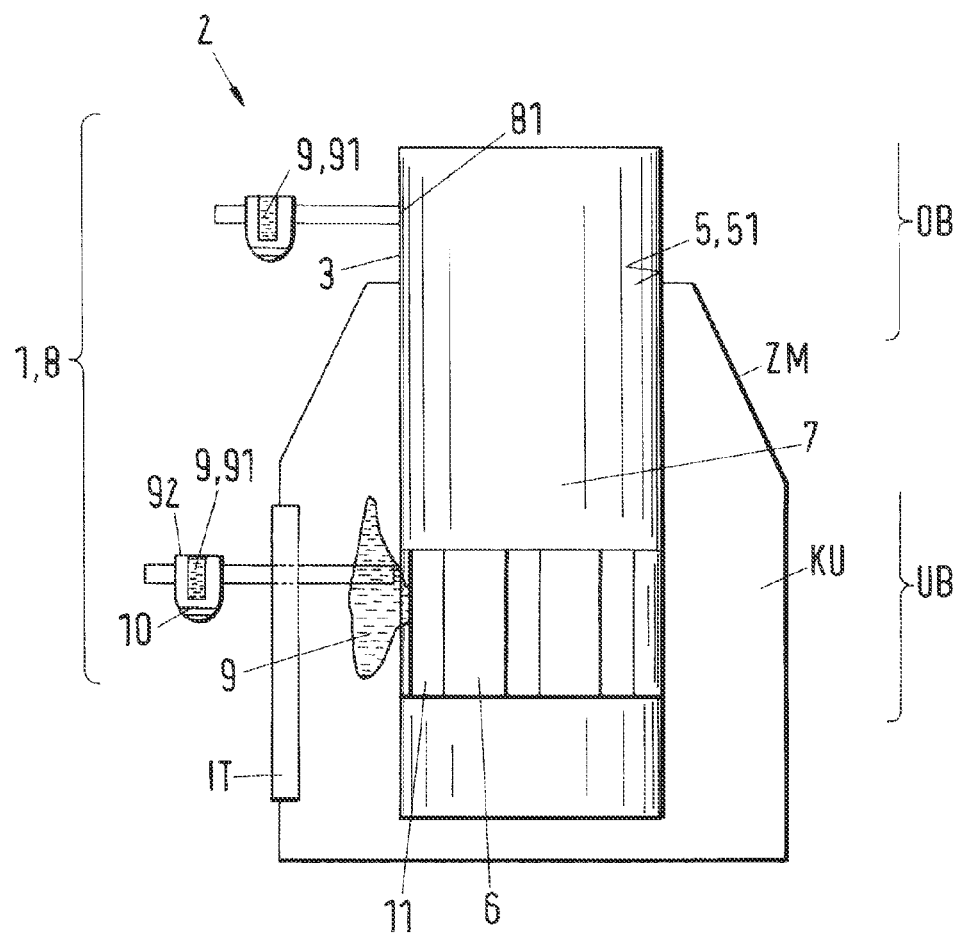
FIG. 3 is a second embodiment in accordance with FIG. 2 having an additional oil collection opening in the upper region of the cylinder.

FIG. 3 shows a second embodiment in accordance with FIG. 2 having an additional oil collection opening 81 in the upper region OB of the cylinder 3. The example of FIG. 3 is therefore almost identical to that of FIG. 1. Therefore lubrication oil 9 can be collected both in the lower region OB of the cylinder and also in the upper region OB of the cylinder with the aid of an embodiment in accordance with FIG. 3.

In this respect it must be explicitly noted at this point that the oil collection openings 81 in the lower region UB do not necessarily have to be arranged in the region of the scavenging slits 11, but in specific cases, for example, can also be arranged above the scavenging slits 11. It is, in particular also possible that the monitoring apparatus 1 in accordance with the invention can be provided at a motor without scavenging slits. For example, at a two-stroke motor or at a four-stroke motor having an inlet valve.

Figure 4:
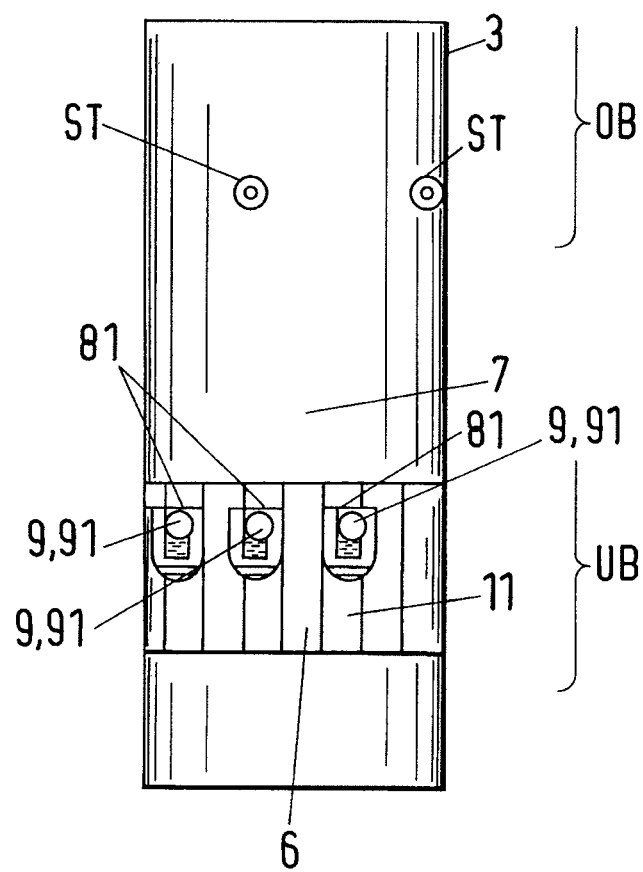
FIG. 4 is a different embodiment in accordance with FIG. 2 having a plurality of oil collection openings in the region of the scavenging slits.

A different embodiment in accordance with FIG. 2 having a plurality of oil collection openings 81 in the region of the scavenging slits 11 is schematically illustrated with reference to FIG. 4, wherein two lubrication oil points ST are also explicitly illustrated exemplary in the upper region OB of the cylinder 3 in this example, whose illustration has been done without for reasons of clarity in the remaining Figures. When, as is the case in the embodiment of FIG. 4, a plurality of oil collection openings 81 are provided in the circumferential direction a homogeneous distribution of the lubrication oil quality and/or the lubrication oil parameters can then be realized, in particular in the circumferential direction, by means of the present invention, particularly well also then when a plurality of lubrication oil points ST are provided and distributed in the circumferential direction at the cylinder 3.

The following FIGS. 5 to 8 show a few specific measurement results which were achieved with the aid of monitoring apparatuses in accordance with the invention in different laboratory experiments.

Figure 5:
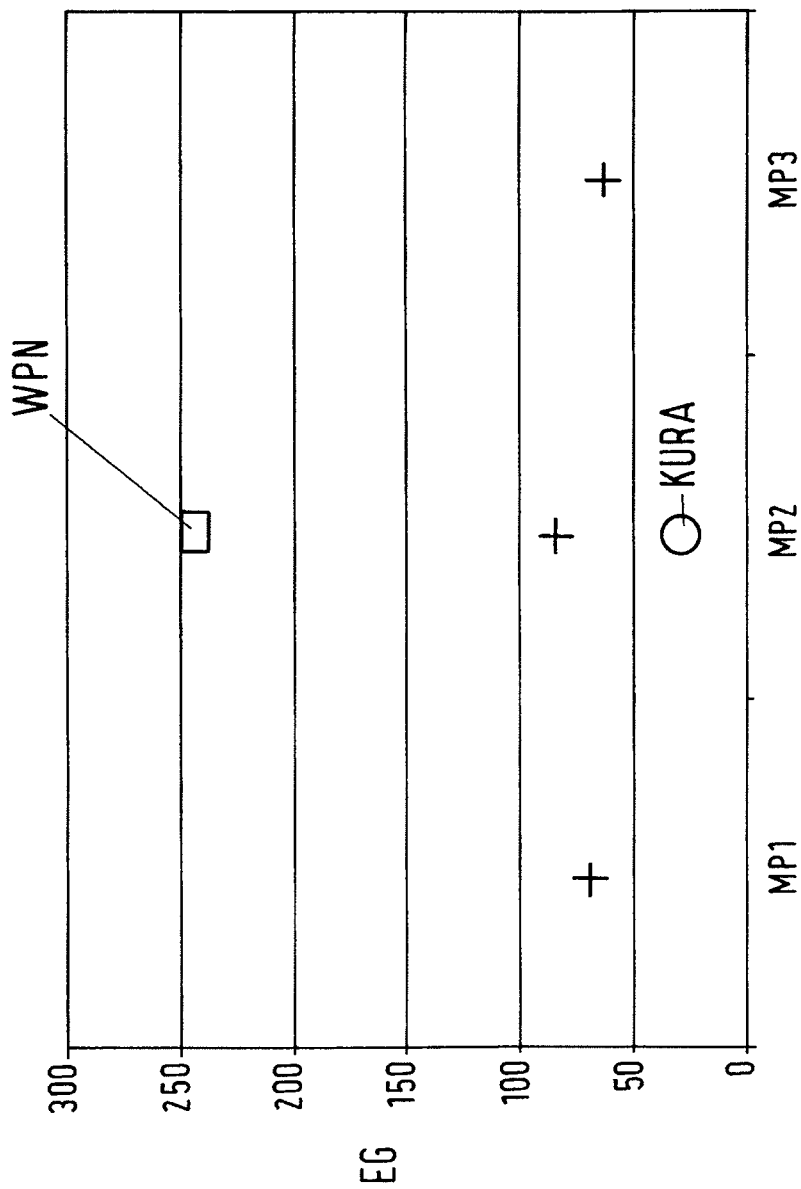
FIG. 5 is a graph showing iron content of a lubrication oil sample in ppm.

FIG. 5 shows the iron content EG of a lubrication oil sample in ppm (parts per million) which was collected at an oil collection opening 81 of a cylinder wall WPN of the cylinder 3. In this respect MP1 is a measurement position 1 which was provided at the scavenging slit 11 in the piston stroke direction not below a lubrication stub. MP2 is a measurement position 2 at the scavenging slit which is located in the piston stroke direction below a lubrication nozzle. And MP3 is a measurement position 3 which is located at a scavenging slit in the piston stroke direction not below a lubrication nozzle.

The measurement points referred to by KURA correspond to a piston lower side space drainage.

FIG. 5 also shows how for a specific motor type equipped with a specific lubrication system and a specific system of piston rings and a cylinder liner processing matching thereto, which has been run in over a specific time of a few thousand operating hours at specific settings of the lubrication system, as well as a specific combination of engine number of rotations and engine load, how the iron content in the lubrication oil sample depends on from where the sample was taken at the motor. The iron content in the lubrication oil sample represents a combination of abrasive and corrosive wear arising during the motor operation. The sample taken at the piston lower side space drainage KUEA has the lowest iron content, while all samples from the measurement positions MP1 to MP3, indicated in FIG. 5 by three crosses in the diagram, taken at the respective scavenging slits have a significantly higher value, and the sample taken from the extraction opening in the cylinder wall has the highest value. The measurement accuracy in the example of FIG. 5 lies at approximately 5 ppm. This is interpreted such that the sample from the extraction opening directly in the cylinder wall corresponds best to the condition of the lubrication oil on the cylinder wall, while the samples taken from the measurement positions MP1 to MP3 at the respective scavenging slits are already mixed with a certain quantity of unused oil which is transported with every piston stroke through the piston rings from the lubrication points, which are located in the upper third of the cylinder liner, downwardly to the scavenging slits and for this reason have a lower iron content, as fresh lubrication oil has an iron content of only approximately 7 ppm. The different iron contents at the measurement positions MP1, MP2 and MP3 show that the lubrication oil has a different quality in dependence on how the measurement position behaves relative to the position of the lubrication points in the cylinder liner for the case considered. The sample from the piston lower side space drainage has the lowest iron content which indicates an even stronger mixing with fresh unused lubrication oil and the sample can also be further contaminated with lubrication oil from neighboring cylinders.

Figure 6:
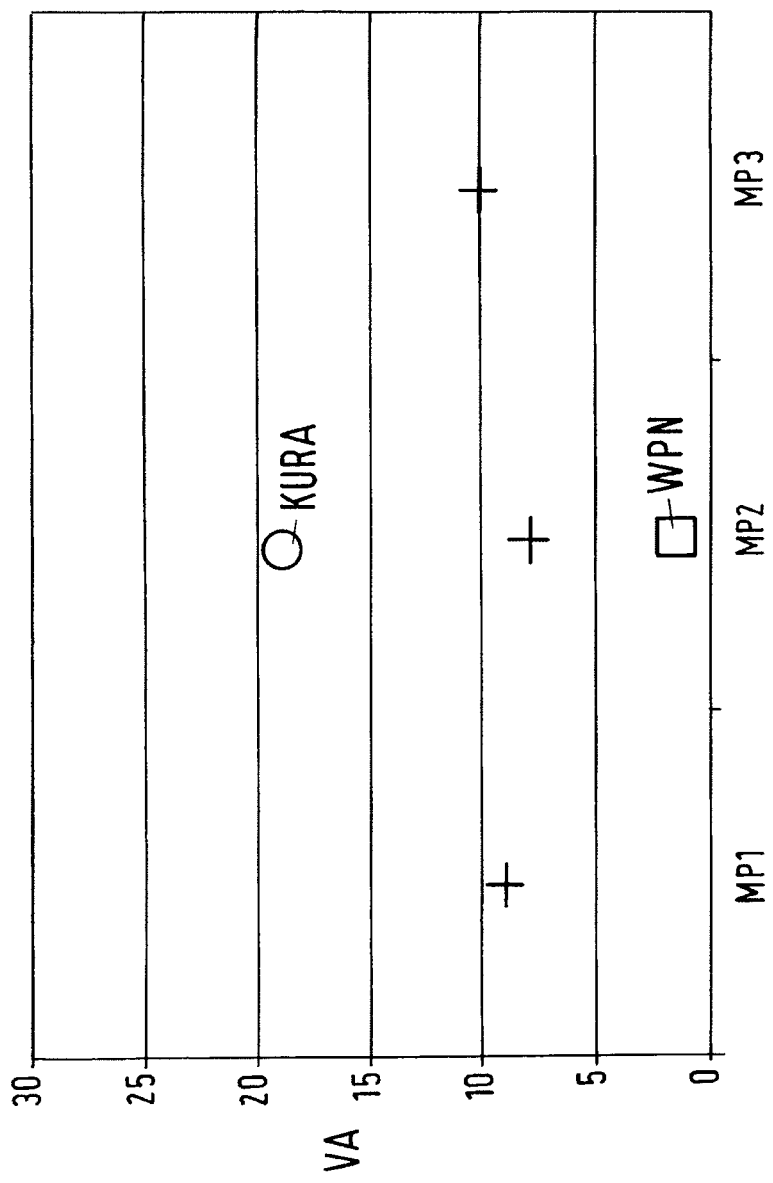
FIG. 6 is a graph showing remaining alkalinity of a lubrication oil sample in milligrams KOH per gram of lubrication oil sample.

In FIG. 6 a measurement of the remaining alkalinity VA of a lubrication oil sample in milligrams KOH per gram lubrication oil sample is illustrated.

In this respect VA is the remaining alkalinity (base number) of the oil sample in milligram KOH per gram oil sample, WPN is the wall sample extraction by means of an oil collection device in the wall of the cylinder. MP1 is the measurement position 1 in a piston stroke direction which is not located below a lubrication nozzle, MP2 is the measurement position 2 in a piston stroke direction located below a lubrication nozzle and MP3 is the measurement position 3 in a piston stroke direction not below a lubrication oil nozzle. MP1, MP2 and MP3 are illustrated in the diagram of FIG. 6 similar to that of FIG. 5 likewise by means of crosses. In this example KURA is also the piston lower side space drainage.

FIG. 6 shows, how for a specific motor type, configured with a specific lubrication system and a specific system of piston rings and a thereto matching cylinder liner processing, which has been run in over a specific time of a few thousand operating hours at certain settings of the lubrication system and also for a specific combination of motor numbers of rotation and motor loads, how the remaining alkalinity in the lubrication oil sample depends on from where the sample was taken in the motor. The alkalinity added to the lubrication oil as an additive in the example of FIG. 6 amounts to 70 milligram KOH per gram of lubrication oil and serves for the neutralization of the sulfuric acid $H_2SO_4$ arising during the motor operation for the combustion of strongly sulfur-containing fuel. The remaining alkalinity in the lubrication oil sample represents the still inherent property of the oil to neutralize sulfuric acid. If the value of the remaining alkalinity in the lubrication oil sample has sunk to zero or towards zero, no or insufficient neutralization takes place and the material of the cylinder liner starts to corrode, whereby the iron content in the lubrication oil sample is increased. The sample taken at the piston lower side space drainage shows the highest still remaining alkalinity, while all samples taken from the measurement positions 1 up to 3 at the respective scavenging slits have a significantly lower value and the samples from the extraction opening in the cylinder wall have a value at approximately zero. The measurement accuracy for the example of FIG. 2 lies at approximately 1.5 milligrams KOH per gram lubrication oil. This result is interpreted such that the sample from the extraction opening directly in the cylinder wall comes closest to the condition of the lubrication oil on the cylinder wall and thereby indicates the danger of corrosion of the cylinder surface, while the sample taken from the measurement positions 1 to 3 at the respective scavenging slits have already been mixed with a certain quantity of unused oil, which is transported with every piston stroke by the piston rings from the lubrication points, which are located in the upper third of the cylinder liner, downwardly to the scavenging slits and for this reason show an increased content of remaining alkalinity. The different contents of remaining alkalinity at the measurement positions 1, 2 and 3 shows that the lubrication oil has a different quality in dependence on how the measurement position behaves relative to the position of the lubrication point in the cylinder liner for the case considered. The sample taken from the position bottom side space drainage has the highest content of remaining alkalinity which indicates a still stronger mixing of fresh, unused lubrication oil and can also be further contaminated with lubrication oil of the neighboring cylinders.

Figure 7:
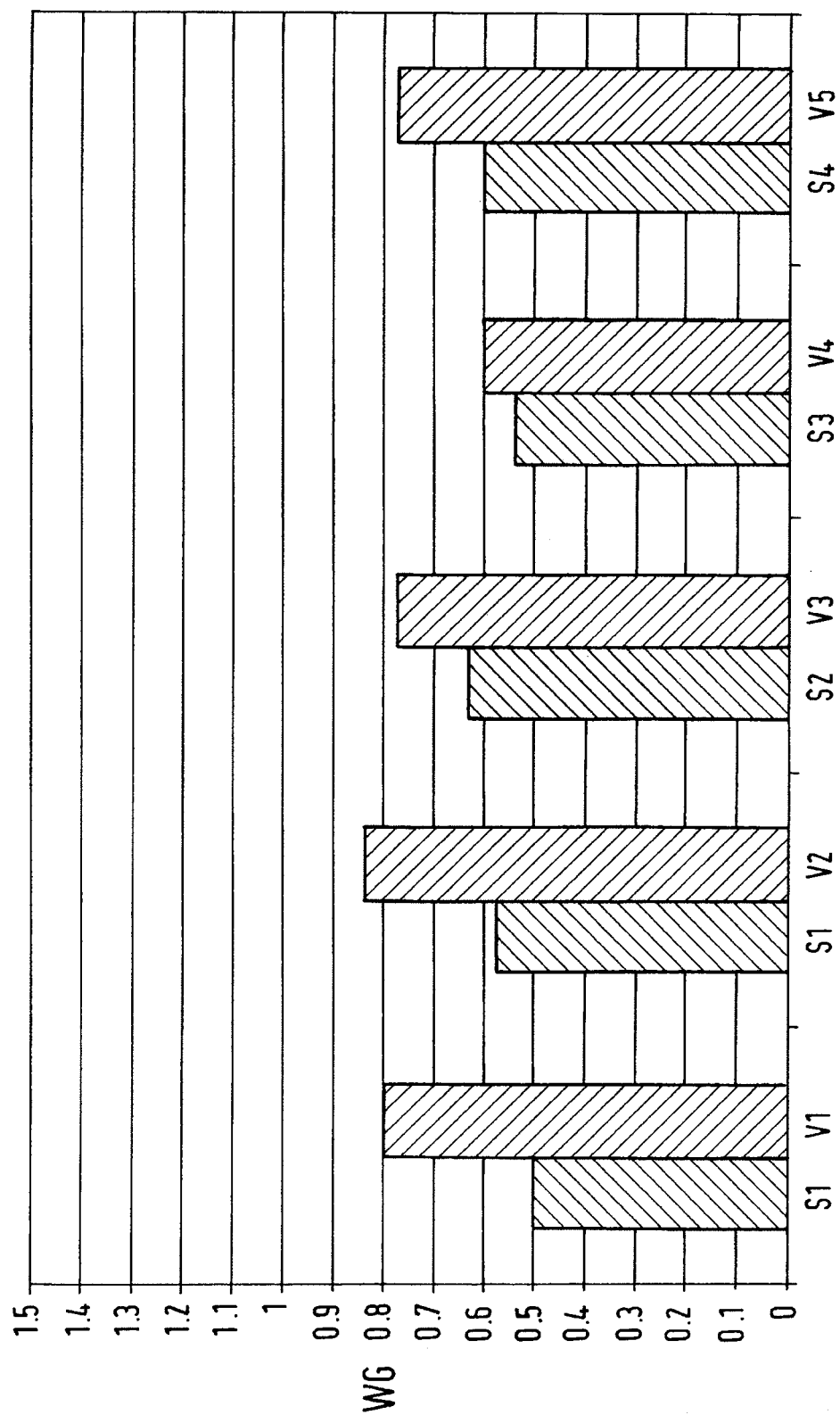
FIG. 7 is a graph showing a first example of a water content of a lubrication oil sample in percent of the sample mass.

FIG. 7 shows a first example of a water content of a lubrication oil sample in percent of the sample mass.

In this respect the denominations in FIG. 7 have the following meaning:

WG=water content of the oil sample in percent of the sample mass
S1=ship motor combination 1
S2=ship motor combination 2
S3=ship motor combination 3
S4=ship motor combination 4
V1=cylinder lubrication variant 1
V2=cylinder lubrication variant 2
V3=cylinder lubrication variant 3
V4=cylinder lubrication variant 4
V5=cylinder lubrication variant 5

FIG. 7 clearly shows that the water content in the lubrication oil sample is formed from the mean value of the samples of the measurement positions MP1 to MP3 described in FIGS. 1 and 2 correlates with the humidity of the environmental air used for the operation of the reciprocating piston internal combustion engine and indeed independent of the ship selected for the measurement (in total four different ones) and independent of the cylinder lubrication variant installed on the motor of the selected ship comprising a specific lubrication system, a specific system of piston rings and a thereto matching cylinder liner processing, as well as the setting of the lubrication system. Apart from the case "S3 V4" the combination of motor number of rotations and motor load was similar for all cases shown in FIG. 7, whereby a load dependence of the water content in the lubrication oil sample could be shown.

Finally, a measurement of a second example of a water content of a lubrication oil sample in percent of the sample mass is illustrated in FIG. 8, wherein WG is again the water content of the oil sample in percent of the sample mass. ZS1 is unused cylinder lubrication oil, ZS2 is cylinder lubrication oil in the stationary operating state and ZS3 is lubrication oil in the transient operation state with increasing load.

Figure 8:
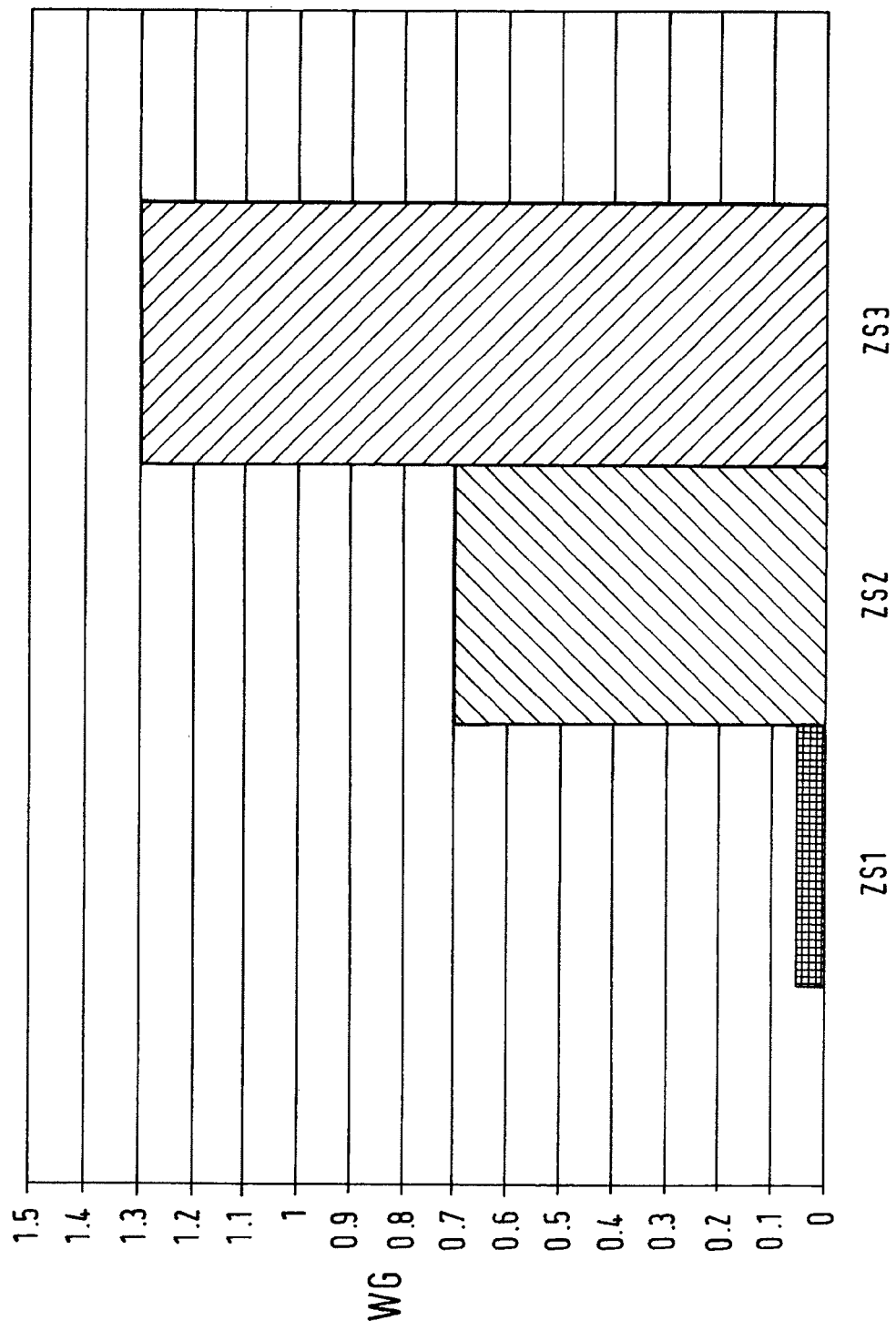
FIG. 8 is a graph showing a second example of a water content of a lubrication oil sample in percent of the sample mass.

FIG. 8 impressively shows that the water content in the lubrication oil sample formed from the mean value of the samples of the measurement positions MP1 to MP3 described in FIGS. 1 and 3 correlates with the type of the motor load which is applied to the motor for constant humidity of the surrounding air for the operation of the reciprocating piston internal combustion engine. A measurement is carried out (cylinder lubrication oil in stationary operating state) for constantly maintained settings of the lubrication system, where the motor was loaded from 25% to 50% of a nominal load in accordance with the propeller law, where the load was then maintained for 40 minutes and the motor was then loaded from 50% to 75% of the nominal load in accordance with the propeller law and the load was then maintained for 40 minutes and finally was loaded to 100% of the nominal load which took a total of four hours. The motor was loaded continuously from 25% to 100% of the nominal load which took approximately 40 minutes for a different measurement with the same motor and the same settings (cylinder lubrication oil in transient operating state with increasing load) at the same day. It is shown that the faster loading of the motor leads to a higher water content in the lubrication oil sample which is considered to be disadvantageous for the wear properties of the cylinder liner.

It is naturally understood that all embodiments described in the framework of this application are to be understood merely by way of example and, in particular also each suitable combination and/or each expansion obvious to the person of ordinary skill in the art.

The invention claimed is:

1. A monitoring apparatus for monitoring a state of wear of a component of a reciprocating piston internal combustion engine comprising:
a cylinder having a cylinder cover and a running surface provided at a cylinder wall of the cylinder; and,
a piston arranged in the cylinder and moveable to and fro in an axial direction along the running surface between a bottom dead center and a top dead center such that the piston, the cylinder cover and the cylinder wall form a combustion space in the cylinder for the combustion of a mixture of a fuel and air,
wherein an oil collection device is provided for the collection of lubrication oil from the cylinder so that a predetermined measured quantity of lubrication oil is suppliable from the cylinder to a measurement device, wherein the measured quantity of lubrication oil is directly suppliable from the running surface of the cylinder and/or is directly suppliable from the combustion space and/or is directly suppliable from a piston ring package of the piston to the oil collection device wherein the measurement device includes an electromagnetic measurement unit, of a magnetic permeability, of an electric DC conductivity and/or of an AC conductivity, and/or of a complex electric conductivity and/or of a complex electric resistance of the collected measured quantity of lubrication oil, and wherein the monitoring apparatus is provided miniaturized directly in the cylinder wall.

2. A monitoring apparatus in accordance with claim 1, wherein the oil collection device includes an oil collection valve actuatable by a control device.

3. A monitoring apparatus in accordance with claim 1, wherein the oil collection device includes an oil collection space which is an integral part of the cylinder wall and lubrication oil collected in the oil collection space is suppliable to the measurement device.

4. A monitoring apparatus in accordance with claim 1, wherein at least two oil collection openings are provided which are arranged at the cylinder displaced from one another in the circumferential direction and/or with regard to the axial direction.

5. A reciprocating piston internal combustion engine, having a monitoring apparatus in accordance with claim 1.

6. The monitoring apparatus of claim 1 wherein the measurement unit is for the amplitude dependent and/or the frequency dependent and/or the frequency independent determination of a capacitance.

7. A monitoring apparatus in accordance with claim 1, wherein the oil collection device includes an oil collection opening which is provided at the cylinder wall between the bottom dead center of the piston and the cylinder cover.

8. A monitoring apparatus in accordance with claim 7, wherein the reciprocating piston internal combustion engine is a longitudinally scavenged internal combustion engine having scavenging slits and a slow running two-stroke large diesel engine and the oil collection opening is arranged in the region of the scavenging slits such that lubrication oil exiting via the scavenging slits is collectable through the oil collection opening.

9. A monitoring apparatus in accordance with claim 7, wherein the oil collection opening is designed such that a lubrication oil flow-rate is settable.

10. A monitoring apparatus in accordance with claim 7, wherein the reciprocating piston internal combustion engine is a four-stroke reciprocating piston internal combustion engine and the oil collection opening is arranged at the cylinder between the position of a crown of the piston in the top dead center and the position of a bottom side of the piston in the bottom dead center such that lubrication oil is collectable from the cylinder through the oil collection opening.

11. The monitoring apparatus of claim 5 wherein the engine is a two-stroke large diesel engine or a four-stroke engine.

12. A monitoring method for monitoring a state of wear of a component of a reciprocating piston internal combustion engine including a cylinder having a cylinder cover and a running surface provided at a cylinder wall of the cylinder, in which cylinder a piston is arranged moveable to and fro in an axial direction along the running surface between a bottom dead center and a top dead center such that the piston, the cylinder cover and the cylinder wall form a combustion space in the cylinder for the combustion of a mixture of a fuel and air, wherein an oil collection device is provided for the collection of lubrication oil from the cylinder and in the operating state a predetermined measured quantity of lubrication oil is supplied from the cylinder to a measurement device, wherein the measured quantity of lubrication oil is directly supplied from the running surface of the cylinder and/or is directly supplied from the combustion space and/or is directly supplied from a piston ring package of the piston to the oil collection device and wherein the measurement device includes an electromagnetic measurement unit, of a magnetic permeability, of an electric DC conductivity and/or of an AC conductivity, and/or of a complex electric conductivity and/or of a complex electric resistance of the collected measured quantity of lubrication oil is carried out.

13. A monitoring method in accordance with claim 12, wherein the oil collection device includes an oil collection opening which is provided at the cylinder wall between the bottom dead center of the piston and the cylinder cover.

14. A monitoring method in accordance with claim 12, wherein the oil collection device includes an oil collection valve actuatable by a control device, and in the operating state a predefined amount of lubricant is led away out of the cylinder.

15. The monitoring method of claim 12 wherein the measurement unit is for the amplitude dependent and/or the frequency dependent and/or the frequency independent determination of a capacitance.

16. A monitoring method in accordance with claim 12, wherein the oil collection device includes an oil collection space which is an integral part of the cylinder wall and lubrication oil collected in the oil collection space is supplied to the measurement device.

17. A monitoring method in accordance with claim 12, wherein at least two oil collection openings are provided which are arranged at the cylinder displaced from one another in the circumferential direction and/or with regard to the axial direction, so that samples of lubrication oil can be taken from different positions in the cylinder.

18. A monitoring method in accordance with claim 12, wherein a maintenance point in time for the maintenance of a predefined engine component is automatically determined.

19. A monitoring method in accordance with claim 12, wherein the reciprocating piston internal combustion engine is controlled and/or regulated in dependence on a measurement result of the collected measured quantity of lubrication oil (9).

20. A monitoring method in accordance with claim 12, wherein the reciprocating piston internal combustion engine is a longitudinally scavenged internal combustion engine having scavenging slits, and the oil collection opening is arranged in the region of the scavenging slits such that lubrication oil exiting via the scavenging slits is collected through the oil collection opening.

21. The monitoring method of claim 20 wherein the engine is a slow running two-stroke large diesel engine.

22. A monitoring method in accordance with claim 12, wherein the oil collection opening is designed such that a lubrication oil flow-rate can be set.

23. The monitoring method of claim 22 wherein the lubrication oil flow-rate can be set automatically.

24. A monitoring method in accordance with claim 12, wherein data recorded with the measurement device are evaluated and consequentially a state of wear of a component of the reciprocating piston internal combustion engine is determined.

25. The monitoring method of claim 24 wherein the data are evaluated by means of a look-up table and/or by means of a predetermined mathematical function and/or by means of a calibration.

26. The monitoring method of claim 24 wherein the state of wear of the piston and/or of a piston ring and/or of the running surface of the cylinder wall and/or of a gas exchange valve and/or of a different engine component is determined.

27. A monitoring apparatus for monitoring a state of wear of a component of a reciprocating piston internal combustion engine comprising:
 a cylinder having a cylinder cover and a running surface provided at a cylinder wall of the cylinder; and,
 a piston arranged in the cylinder and moveable to and fro in an axial direction along the running surface between a bottom dead center and a top dead center such that the piston, the cylinder cover and the cylinder wall form a combustion space in the cylinder for the combustion of a mixture of a fuel and air,
 wherein an oil collection device is provided for the collection of lubrication oil from the cylinder so that a predetermined measured quantity of lubrication oil is suppliable from the cylinder to a measurement device, wherein the measured quantity of lubrication oil is directly suppliable from the running surface of the cylinder and/or is directly suppliable from the combustion space and/or is directly suppliable from a piston ring package of the piston to the oil collection device and wherein the measurement device includes an X-ray measurement unit.

28. The monitoring apparatus of claim 27 wherein the X-ray measurement unit is for the determination of a transmission property and/or of an absorption property and/or of a reflection property and/or of a fluorescence property of the collected measured quantity of lubrication oil (9).

29. A monitoring apparatus for monitoring a state of wear of a component of a reciprocating piston internal combustion engine comprising:
 a cylinder having a cylinder cover and a running surface provided at a cylinder wall of the cylinder; and,
 a piston arranged in the cylinder and moveable to and fro in an axial direction along the running surface between a bottom dead center and a top dead center such that the piston, the cylinder cover and the cylinder wall form a combustion space in the cylinder for the combustion of a mixture of a fuel and air,
 wherein an oil collection device is provided for the collection of lubrication oil from the cylinder so that a predetermined measured quantity of lubrication oil is suppliable from the cylinder to a measurement device, wherein the measured quantity of lubrication oil is directly suppliable from the running surface of the cylinder and/or is directly suppliable from the combustion space and/or is directly suppliable from a piston ring package of the piston to the oil collection device and wherein the measurement device includes an optical measurement unit for the determination of an optical transmission property and/or of an optical absorption property and/or of an optical reflection property and/or of an optical fluorescence property of the collected measured quantity of lubrication oil.

30. The monitoring apparatus of claim 29 wherein the optical measurement unit is an infrared measurement unit and/or an ultraviolet measurement unit.

31. A monitoring apparatus for monitoring a state of wear of a component of a reciprocating piston internal combustion engine comprising:
 a cylinder having a cylinder cover and a running surface provided at a cylinder wall of the cylinder; and,
 a piston arranged in the cylinder and moveable to and fro in an axial direction along the running surface between a bottom dead center and a top dead center such that the piston, the cylinder cover and the cylinder wall form a combustion space in the cylinder for the combustion of a mixture of a fuel and air,
 wherein an oil collection device is provided for the collection of lubrication oil from the cylinder so that a predetermined measured quantity of lubrication oil is suppliable from the cylinder to a measurement device, wherein the measured quantity of lubrication oil is directly suppliable from the running surface of the cylinder and/or is directly suppliable from the combustion space and/or is directly suppliable from a piston ring package of the piston to the oil collection device and wherein the measurement device includes a chemical measurement unit for the determination of a chemical composition of the collected measured quantity of lubrication oil.

32. A monitoring apparatus for monitoring a state of wear of a component of a reciprocating piston internal combustion engine comprising:
 a cylinder having a cylinder cover and a running surface provided at a cylinder wall of the cylinder; and,
 a piston arranged in the cylinder and moveable to and fro in an axial direction along the running surface between a bottom dead center and a top dead center such that the piston, the cylinder cover and the cylinder wall form a combustion space in the cylinder for the combustion of a mixture of a fuel and air,
 wherein an oil collection device is provided for the collection of lubrication oil from the cylinder so that a predetermined measured quantity of lubrication oil is suppliable from the cylinder to a measurement device, wherein the measured quantity of lubrication oil is directly suppliable from the running surface of the cylinder and/or is directly suppliable from the combustion space and/or is directly suppliable from a piston ring package of the piston to the oil collection device and wherein the measurement device includes a measurement system for the determination of a content of water and/or of a content of metal and/or for the determination of a content of phosphor and/or of sulfur of the collected measured quantity of lubrication oil.

33. The monitoring apparatus of claim 32 wherein the metal content to be determined is of iron and/or of chromium and/or of vanadium.

34. A monitoring method for monitoring a state of wear of a component of a reciprocating piston internal combustion engine including a cylinder having a cylinder cover and a running surface provided at a cylinder wall of the cylinder, in which cylinder a piston is arranged moveable to and fro in an axial direction along the running surface between a bottom dead center and a top dead center such that the piston, the cylinder cover and the cylinder wall form a combustion space in the cylinder for the combustion of a mixture of a fuel and air, wherein an oil collection device is provided for the collection of lubrication oil from the cylinder and in the operating state a predetermined measured quantity of lubrication oil is supplied from the cylinder to a measurement device, wherein the measured quantity of lubrication oil is directly supplied from the running surface of the cylinder and/or is directly supplied from the combustion space and/or is directly supplied from a piston ring package of the piston to the oil collection device and wherein the measurement device includes an X-ray measurement unit.

35. The monitoring method of claim 34 wherein a determination of a transmission property and/or of an absorption property and/or of a reflection property and/or of a fluorescence property of the collected measured quantity of lubrication oil is carried out by the X-ray measurement unit.

36. A monitoring method for monitoring a state of wear of a component of a reciprocating piston internal combustion engine including a cylinder having a cylinder cover and a running surface provided at a cylinder wall of the cylinder, in which cylinder a piston is arranged moveable to and fro in an axial direction along the running surface between a bottom dead center and a top dead center such that the piston, the cylinder cover and the cylinder wall form a combustion space in the cylinder for the combustion of a mixture of a fuel and air, wherein an oil collection device is provided for the collection of lubrication oil from the cylinder and in the operating state a predetermined measured quantity of lubrication oil is supplied from the cylinder to a measurement device, wherein the measured quantity of lubrication oil is directly supplied from the running surface of the cylinder and/or is directly supplied from the combustion space and/or is directly supplied from a piston ring package of the piston to the oil collection device and wherein the measurement device includes an optical measurement unit.

37. The monitoring method of claim 36 wherein a determination of an optical transmission property and/or of an optical absorption property and/or of an optical reflection property and/or of an optical fluorescence property of the collected measured quantity of lubrication oil is carried out by the optical measurement unit and wherein an infrared measurement unit and/or an ultraviolet measurement unit is used as the optical measurement unit.

38. A monitoring method for monitoring a state of wear of a component of a reciprocating piston internal combustion engine including a cylinder having a cylinder cover and a running surface provided at a cylinder wall of the cylinder, in which cylinder a piston is arranged moveable to and fro in an axial direction along the running surface between a bottom dead center and a top dead center such that the piston, the cylinder cover and the cylinder wall form a combustion space in the cylinder for the combustion of a mixture of a fuel and air, wherein an oil collection device is provided for the collection of lubrication oil from the cylinder and in the operating state a predetermined measured quantity of lubrication oil is supplied from the cylinder to a measurement device, wherein the measured quantity of lubrication oil is directly supplied from the running surface of the cylinder and/or is directly supplied from the combustion space and/or is directly supplied from a piston ring package of the piston to the oil collection device and wherein the measurement device includes a chemical measurement unit and a determination of a chemical composition of the collected measured quantity of lubrication oil is carried out.

39. A monitoring method for monitoring a state of wear of a component of a reciprocating piston internal combustion engine including a cylinder having a cylinder cover and a running surface provided at a cylinder wall of the cylinder, in which cylinder a piston is arranged moveable to and fro in an axial direction along the running surface between a bottom dead center and a top dead center such that the piston, the cylinder cover and the cylinder wall form a combustion space in the cylinder for the combustion of a mixture of a fuel and air, wherein an oil collection device is provided for the collection of lubrication oil from the cylinder and in the operating state a predetermined measured quantity of lubrication oil is supplied from the cylinder to a measurement device, wherein the measured quantity of lubrication oil is directly supplied from the running surface of the cylinder and/or is directly supplied from the combustion space and/or is directly supplied from a piston ring package of the piston to the oil collection device and wherein a content of water and/or a content of metal, and/or a content of phosphor and/or of sulfur of the collected measured quantity of lubrication oil is determined by the measurement device.

40. The monitoring method of claim 39 wherein the metal content to be determined is of iron and/or of chromium and/or of vanadium.

41. A monitoring method for monitoring a state of wear of a component of a reciprocating piston internal combustion engine including a cylinder having a cylinder cover and a running surface provided at a cylinder wall of the cylinder, in which cylinder a piston is arranged moveable to and fro in an axial direction along the running surface between a bottom dead center and a top dead center such that the piston, the cylinder cover and the cylinder wall form a combustion space in the cylinder for the combustion of a mixture of a fuel and air, wherein an oil collection device is provided for the collection of lubrication oil from the cylinder and in the operating state a predetermined measured quantity of lubrication oil is supplied from the cylinder to a measurement device, wherein the measured quantity of lubrication oil is directly supplied from the running surface of the cylinder and/or is directly supplied from the combustion space and/or is directly supplied from a piston ring package of the piston to the oil collection device and wherein an evaluation of the measurement of the collected measured quantity of lubrication oil is carried out for each engine cycle.

42. A monitoring method for monitoring a state of wear of a component of a reciprocating piston internal combustion engine including a cylinder having a cylinder cover and a running surface provided at a cylinder wall of the cylinder, in which cylinder a piston is arranged moveable to and fro in an axial direction along the running surface between a bottom dead center and a top dead center such that the piston, the cylinder cover and the cylinder wall form a combustion space in the cylinder for the combustion of a mixture of a fuel and air, wherein an oil collection device is provided for the collection of lubrication oil from the cylinder and in the operating state a predetermined measured quantity of lubrication oil is supplied from the cylinder to a measurement device, wherein the measured quantity of lubrication oil is directly supplied from the running surface of the cylinder and/or is directly supplied from the combustion space and/or is directly supplied from a piston ring package of the piston to the oil collection device and wherein a predetermined measured quantity of lubrication oil is collected during a predetermined number of engine cycles, and a measurement is carried out and evaluated on the predetermined measured quantity of lubrication oil.

* * * * *